(12) United States Patent
Chattaraj et al.

(10) Patent No.: US 7,790,461 B2
(45) Date of Patent: Sep. 7, 2010

(54) NANO-EMULSION TECHNOLOGY FOR DRUG ELUTION

(75) Inventors: Sarnath Chattaraj, Simi Valley, CA (US); Poonam S. Gulati, La Canada, CA (US); Eugene Levin, West Hills, CA (US); Elango S. Minnoor, Northridge, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 436 days.

(21) Appl. No.: 12/005,952

(22) Filed: Dec. 28, 2007

(65) Prior Publication Data

US 2009/0169624 A1 Jul. 2, 2009

(51) Int. Cl.
*G01N 33/15* (2006.01)
(52) U.S. Cl. .............................. 436/8; 436/17; 514/772; 514/179
(58) Field of Classification Search .................. 436/8, 436/17; 514/772, 179
See application file for complete search history.

(56) References Cited

U.S. PATENT DOCUMENTS

| | | |
|---|---|---|
| 6,308,584 B1 | 10/2001 | Benz |
| 2002/0138123 A1 | 9/2002 | Casas-Bejar et al. |

2006/0260421 A1  11/2006  Sekizawa et al.

FOREIGN PATENT DOCUMENTS

WO     2005051544     6/2005

OTHER PUBLICATIONS

International Search Report mailed Nov. 20, 2008, International application No. PCT/US2008/009085, International filing date Jul. 25, 2008.
Noory et al., "Steps for development of a dissolution test for sparingly water-soluble drug products," American Pharmaceutical Review, vol. 5, No. 4, Jan. 1, 2002, pp. 16-20.
Shirakura et al., "Synergistic effect of d-limonene and ethanol on the transdermal permeation of NB-818," Drug Development and Industrial Pharmacy, New York, NY, vol. 21, No. 4, Jan. 1, 1995, pp. 411-425.
Behan et al., "Perfume interactions with sodium dodecyl sulphate solutions," International Journal of Cosmetic Science, Kluwer Academic Publishers, Dordrecht NL, vol. 9, No. 6, Jan. 1, 1987, pp. 261-268.

*Primary Examiner*—Jill Warden
*Assistant Examiner*—Timothy G Kingan
(74) *Attorney, Agent, or Firm*—Gates & Cooper LLP

(57) ABSTRACT

Embodiments of the invention provide to apparatuses and media used in drug elution studies and methods for making and using them. One embodiment of the invention is a drug elution method that can be used for in-vitro studies of a matrix impregnated with a compound such as a drug blended polymer matrix. Such methods and materials can be used for example to assess and control the manufacturing process variability of drug eluting implantable devices such as cardiac leads.

20 Claims, 6 Drawing Sheets

NANO-EMULSION TECHNOLOGY FOR DRUG ELUTION

CROSS REFERENCE TO RELATED APPLICATIONS

This application is related to U.S. patent application Ser. No. 11/881,074 filed Jul. 25, 2007, the contents of which are incorporated by reference.

BACKGROUND OF THE INVENTION

1. Field of the Invention

The present invention relates to media used in drug elution studies and methods for making and using them.

2. Description of Related Art

The implantation of a medical device into a patient's body can cause the body to exhibit adverse physiological reactions ranging from infections to the formation of emboli or clots in blood vessels. One approach to address such reactions and improve the biocompatibility of such medical devices is to incorporate bioactive or pharmacological agents such as steroids, and/or antibiotics and/or anticoagulants onto a surface of these devices. Once implanted, these agents can then elute into the in vivo environment at the site of implantation and modify the physiological response.

Exemplary medical procedures that involve the implantation of medical devices include those designed to modulate cardiac physiology. For example, a variety of systems that use one or more pacing leads with electrodes such as cardiac rhythm management (CRM) systems and various techniques for implanting these lead systems in contact body tissue such as the heart, have been developed. In this context, the safety, efficacy and longevity of an electrical pulse generator of a CRM depends, in part, on the performance of the associated cardiac lead(s) used in conjunction with the pulse generator. For example, various properties of the lead and electrodes will result in a characteristic impedance and stimulation threshold. Stimulation threshold is the energy required in a stimulation pulse to depolarize, or "capture," the heart tissue. A relatively high impedance and low threshold is desired to minimize the current drawn from a pulse generator battery in delivering a stimulation pulse. Another example may be when implanting a medical device, it can result in infections in the area of infections. Such infections can be reduced by coating or otherwise combining an antibiotic with the implanted device.

One factor that can affect the stimulation threshold, particularly during the first several weeks after implantation of a lead, is the natural immunological response of the body to the lead as a foreign object. The presence of the lead activates macrophages, which attach themselves to the surface of the lead and any electrodes and form multi-nucleated giant cells. These cells, in turn, secrete various substances, such as hydrogen peroxide as well as various enzymes, in an effort to dissolve the foreign object. Such substances, while intending to dissolve the foreign object, also inflict damage to the surrounding tissue. When the surrounding tissue is the myocardium, these substance cause necrosis. These areas of necrosis, in turn, impair the electrical characteristics of the electrode-tissue interface. Consequently pacing thresholds rise. Even after the microscopic areas of tissue die the inflammatory response continues and approximately seven days after implant the multi-nucleated giant cells cause fibroblasts to begin laying down collagen to replace the necrotic myocardium. Eventually, on the order of three weeks after implant, the lead and its electrodes can be encapsulated by a thick layer of fibrotic tissue. Typically, the inflammatory response ends at this time. The fibrotic encapsulation of the lead and its electrodes, however, remains. Since the fibrotic tissue is not excitable tissue, an elevated stimulation threshold can persist due to the degraded electrical properties of the electrode-tissue interface.

One means of modulating this inflammatory response in implanted cardiac rhythm management systems has been to provide a drug near the electronic lead to mitigate the inflammatory tissue reaction described above. In particular, it has been found devices designed to elute an anti-inflammatory agent, such as a glucocorticoid steroid, minimize tissue irritation, help reduce or eliminate threshold peaking and further assist in maintaining low acute and chronic pacing thresholds. A considerable breakthrough in the development of low threshold electrode technology occurred with the invention of the steroid eluting pacing electrode of Stokes U.S. Pat. No. 4,506,680 and related Medtronic U.S. Pat. Nos. 4,577,642, and 4,606,118. Steroid, it is believed, inhibits the inflammatory response by inhibiting the activation of the macrophages. Because they do not form multi-nucleated giant cells, the subsequent release of substances to dissolve the object and which also destroy the surrounding tissue is prevented. Thus, the necrosis of any tissue by the inflammatory response is minimized as well as the formation of the fibrotic capsule. Minimizing such adverse reactions is highly desirable because it also minimizes the concomitant deterioration of the electrical characteristics of the electrode-tissue interface. The incorporation of a compound such as a steroid that elutes at the site of implantation permits pacing leads to have a source impedance substantially lower as compared to leads featuring similarly sized solid electrodes. Consequently, electronic leads which can elute compounds such as steroids also present significantly lower peak and chronic pacing thresholds than similarly sized electrodes and have therefore been adapted for patient treatment in a variety of contexts.

Implantable compositions which elute a steroid can include a drug blended with a polymeric material such as dexamethasone impregnated within a silicone polymer, a blended composition that is designed to slowly elute the steroid out of the polymer and into the surrounding tissue. Incorporating a drug such as a steroid into a device so that it will elute from a device upon implantation, however, increases the complexity of electronic device production as compared to non-steroid eluting devices. One potential area of difficulty in this context is the possibility of variable manufacturing processes and the potential associated effects on elution kinetics. In this context, methods and materials that allow artisans to readily examine the drug elution properties of electronic devices and other drug eluting medical devices are highly desirable. Such methods and materials can be used for example to assess manufacturing process variability of drug eluting implants and the associated quality control of such processes. Moreover, while real time in vivo elution studies may be necessary to gain a comprehensive mechanistic understanding of the modulation of the physiological reactions observed with implantation, such real time elution tests can be on the order of weeks or months. Consequently, accelerated in-vitro tests that correlate with such tests are important for manufacturing and quality control processes. For this reason, methods and materials such as media and apparatuses that can be used to assess and control the manufacturing process variability of drug eluting implantable devices are highly desirable.

SUMMARY OF THE INVENTION

Embodiments of the invention provide apparatuses and media useful for drug elution studies and methods for making and using them. The media and associated methods disclosed herein are designed for the elution of agents impregnated within a polymer matrix. Such methods and materials can be used, for example, to assess and control the manufacturing process variability of drug eluting implantable devices such as cardiac leads.

One embodiment of the invention is a drug elution method that can be used for in-vitro studies of a matrix impregnated with a compound such as a drug blended polymer matrix. Illustrative embodiments of the invention include methods that use a unique dissolution media to observe the elution of dexamethasone acetate from a blended polymer, a matrix that can be used for example with drug loaded pace maker leads. This dissolution media uses a combination of constituents designed to elute compounds from within a matrix effectively and efficiently over a relatively short period of time. This dissolution media and methods for using it consequently provide an in-vitro platform for product development and quality control, particularly in the production of drug coated medical devices.

An illustrative embodiment of the invention is a method for observing the elution of a compound from a matrix using a form of a nano-emulsion technique, the method comprising exposing the matrix comprising the compound to a solution comprising: phosphate buffered saline having a pH range of pH 5 to pH 7; 1-9% limonene; 0.3-9% sodium dodecyl sulfate; and 0.5-15% lower alkanol; and then assaying the solution for the presence of the compound so as to observe the elution of the compound from the matrix into the solution (e.g. via a chromatographic separation technique such as HPLC). In some embodiments of the invention, the lower alkanol is ethanol or n-butanol. In certain embodiments, the solution comprises phosphate buffered saline at pH 6; 3-5% limonene; 3-5% sodium dodecyl sulfate; and 1-3% n-butanol.

The methods of the invention can be used to study the elution of a wide variety of compounds from a wide variety of matrices. For example, the method can be used to study a plastic or other polymeric matrix having the compound impregnated, coated or embedded therein. In an illustrative embodiment, the matrix can comprise a polymer such as a silicone polymer and the compound can comprise a steroid, an anti-coagulant an antibiotic, or an anti-inflammatory agent. In an illustrative embodiment provided in the examples below, the matrix is a biomedical grade silicone polymer impregnated with dexamethasone acetate. Typically, the matrix and the compound are adapted for implantation in vivo, for example as part of an electronic lead of a pacemaker.

In typical embodiments of the invention, the methods are adapted to facilitate processes such as the product development and quality control of implantable drug coated medical devices. In such embodiments, the method can be practiced on a plurality of matrices produced according to a uniform manufacturing process, typically one designed to produce a plurality of matrices that elute the compound at the same rate. Optionally, the method can include the step of comparing the elution rates of two or more of plurality of matrices to determine if the two or more matrices have the same or different elution rates.

A related embodiment of the invention is a composition of matter comprising a solution of phosphate buffered saline having a pH range of pH 5 to pH 7; 1-9% limonene; 0.3-9% sodium dodecyl sulfate; and 0.5-15% lower alkanol. In certain embodiments of this composition, the lower alkanol is ethanol or n-butanol. Optionally in this composition, the solution comprises phosphate buffered saline having a pH of 6, 3-5% limonene; 3-5% sodium dodecyl sulfate; and 1-3% n-butanol.

In some embodiments of the invention, the composition of matter further comprises a matrix impregnated with an elutable agent comprising a steroid, an anti-coagulant an antibiotic, or an anti-inflammatory agent. Optionally for example, the matrix is a polymer matrix impregnated with dexamethasone acetate. In one illustrative embodiment of the invention, the composition of matter further comprises a polymer matrix adapted for use as part of a cardiac lead.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE EMBODIMENTS

Figure 1A:
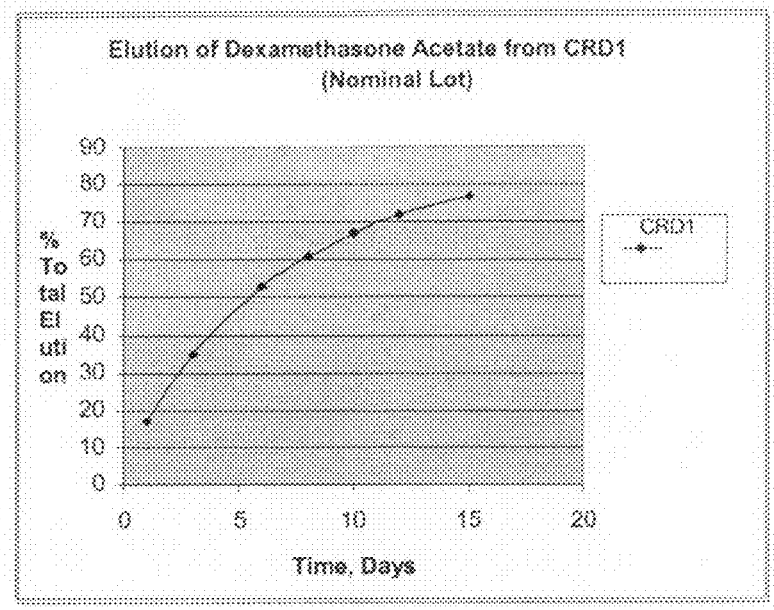
FIGS. 1A and 1B show typical plots of the elution of dexamethasone acetate from Controlled Release Devices (CRD).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

A. Methods and Media for Observing Drug Elution from a Matrix

The invention disclosed herein has a number of embodiments. One embodiment of the invention is a drug elution method that can be used for in-vitro studies of a matrix impregnated with a compound such as a drug blended polymer matrix. Specific embodiments of the invention include methods that use a unique dissolution media to observe the elution of dexamethasone acetate from a drug blended polymer matrix, a matrix that is used for example with drug loaded pace maker leads. This dissolution media uses a combination of constituents designed to elute compounds from within a matrix effectively and efficiently over a relatively short period of time. This dissolution media and methods for using it consequently provide an in-vitro platform for product development and quality control, particularly in the production of drug coated medical devices.

In the examples below, the disclosure provides illustrative embodiments of the methods of invention that examine the elution of dexamethasone from a polymeric silicone matrix. This example provides an illustration of the power of the methods of the invention, in particular in view of the fact that the elution of dexamethasone acetate from silicone polymer/drug coated pace maker leads is known to be minimal in conventional solvents. In this context, the elution media dissolution solution includes limonene. As is known in the art, limonene assumes isomeric forms such as (R)-(+)-Limonene and (S)-(−)-limonene. Optionally the limonene used in embodiments of the invention is a single isomer or alternatively a combination of limonene isomers. In typical embodiments of the invention, a single limonene isomer is used which is (R)-(+)-limonene. The addition of limonene provides a unique dissolution media additive that dramatically increases the dissolution of dexamethasone acetate from matrices such as the drug coated pace maker leads. Without being bound by a specific scientific theory, it appears that the limonene swells the polymer and helps in eluting a drug such as dexamethasone acetate from a matrix such as drug coated pace maker leads. As any matrix comprising a compound can be tested using the disclosed methods and materials, the methods of the invention are applicable to a wide variety of other contexts where it is desirable to observe the elution of a compound from a matrix.

Embodiments of the invention include an elution media containing a cosolvent in the form of a lower alkanol. As used herein the term "alkanol" refers to alkanes (saturated hydrocarbons with straight or branched chain structures, with general formula $C_nH_{2n+2}$) having a hydroxyl group (—OH) moiety. As used herein the term "lower alkanol" refers to alkanols having 1-8 carbon atoms such as methanol, ethanol, propanol, butanol, pentanol, hexanol, heptanol, octanol or mixtures thereof. The term "lower alkanol" includes both straight chain alkanols having 1-8 carbon atoms such as 1-propanol (also known in the art as n-propanol) and 1-butanol (also known in the art as n-butanol) etc. as well as isomers such as isopropanol, isobutanol, sec-butanol, tert butanol etc. In illustrative embodiments of the invention, the lower alkanol is ethanol or n-butanol.

Surprisingly, the addition of a lower alkanol cosolvent provides an elution media with unexpectedly desirable elution properties, for example an enhanced ability to elute agents that are tightly complexed within a matrix, for example a drug complexed within a polymer matrix. Without being bound by a specific scientific theory, it is believed that the lower alkanol cosolvent functions to stabilize the micelle structures formed by the components of the elution media and/or allow the formation of smaller micelle structures in a manner that allows the micelles to penetrate deeper into a matrix structure and elute an agent impregnated therein. In addition (and perhaps consequently), the inclusion of a lower alkanol cosolvent allows the elution media to include higher concentrations of both SDS and limonene.

The methods and compositions of the invention can be used in a variety of contexts and are particularly well suited for studies of materials variations that can occur for example within a batch of processed materials and/or between batches of processed material. The term "batch" is used according to its art accepted meaning and refers to a specific quantity of a drug or other material produced (typically according to a single manufacturing order during the same cycle of manufacture) and intended to have uniform character and quality, within specified limits. As shown in the examples below, this dissolution media is proven to be discriminatory for detecting process variations in manufacturing processes.

While the methods of the invention can be used to assess the elution of a wide variety of compounds from a wide variety of matrices, these methods of the invention are particularly useful in the context of the manufacture of drug eluting implantable medical devices. For example, the safety and efficacy of drug coated pace maker leads are readily evaluated using the unique dissolution methods and materials disclosed herein. In contrast, due to the extended release nature of the product and also due to the poor solubility of dexamethasone acetate, the elution of the drug is observed to be minimal in conventional dissolution media, for example a media that utilizes just a surfactant.

A typical embodiment of the invention is a method for observing the elution of a compound from a matrix comprising the compound into a solution. In typical embodiments of this method, the solution comprises phosphate buffered saline having a pH range of pH 5 to pH 7; 1-9% limonene; 0.3-9% sodium dodecyl sulfate and 0.5-15% lower alkanol. In an exemplary embodiment of this method, the solution comprises phosphate buffered saline having a pH of 6, 3-6% limonene; 3-6% sodium dodecyl sulfate, and 1-3% 1-butanol. Typically, the method comprises combining the matrix comprising the compound with the solution and then observing the elution of the compound from the matrix into the solution over time.

This solution and method can be used in the evaluation of manufacturing processes, for example to confirm that samples from various batches have elution properties within a set of characteristic parameters. Some embodiments of the invention may include a 1-9% limonene solution and 0.5-15% lower alkanol as well as other components known in the art and used in elution studies, for example acetate buffer having a pH range of pH 5 to pH 7 and/or anionic (e.g. sodium dodecyl sulfate), cationic (e.g. Cetyl trimethyl ammonium bromide—CTAB) and non-ionic (e.g. Solutol HS 15-polyoxyethylene esters of 12-hydroxystearic acid, Tween 80) surfactants.

Embodiments of the method can be manipulated by modifying the conditions under which elution is observed, for example, by observing elution at a specific solution temperature or temperature range, e.g. at 25, 30, 37, 40 or 45 degrees centigrade or between 25 and 45 degrees centigrade. In addition, typical embodiments of the invention include the steps of agitating the solution with a stirring device, shaker or use a flow through device like USP apparatus 4. Typically, the volume of the solution used in such methods is between 50 and 150 milliliters (e.g. 50, 75, 100, or 125 milliliters). In some embodiments of the invention, the specific formulation of the media is selected for specific elution characteristics, for example, an ability to elute at least 50% of dexamethasone acetate impregnated within a polymeric silicone matrix in 72 hours at 37 degrees centigrade.

In describing this invention, the term "matrix" simply means any material in which a compound can be coated on to, and/or combined with and/or embedded within and/or enclosed within. Similarly, the "matrix comprising the compound" is a material having a compound such as a steroid and/or anticoagulant and/or antibiotic or the like loaded and/or coated on it and/or embedded within it and/or enclosed within it. Such methods for observing the elution of a compound from a matrix by exposing the compound to a solution and then observing the presence of the compound in the solution over a period of time can be used to observe a wide variety of matrices and compounds. Such assays can be used to determine what percentage of a compound (e.g. 0% up to 100% of a drug loaded compound) is eluted under specific conditions (e.g. concentration of various components of the media and/or pH and/or temperature etc.) over various periods of time (e.g. 1 minute, 1 hour, 1 day or 1 week etc.).

Elution of a compound from a wide variety of matrices are known in the art can be observed in the methods of the invention. In typical embodiments of the invention, the matrix is an implantable polymer matrix. Typically, polymer matrices observed in the methods of the invention are biocompatible and designed to minimize irritation at the site of implantation. In certain embodiments of the invention, the polymer may be either a biostable or a bioabsorbable polymer depending on the desired rate of release or the desired degree of polymer stability. Biostable polymers such as polyurethanes, silicones, and polyesters are used in certain embodiments of the invention. In the examples provided below, the illustrative matrix used to demonstrate embodiments of the invention is a biomedical silicone polymer impregnated with dexamethasone. Other polymers can also be used in certain embodiments of the invention such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose. Bioabsorbable polymers include poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. In other embodiments of the invention, the matrix can be a metal such as one of the metals typically used in portions of implantable medical devices that are exposed to living tissue.

A wide variety of compounds can be coated on to, and/or combined with and/or embedded within and/or enclosed within a matrix to produce a matrix comprising the compound. For example, the compound used in the present invention can be virtually any compound which possesses desirable therapeutic characteristics for implantation. In some embodiments, the compound is a glucocorticoid such as dexamethasone, dexamethasone sodium phosphate, dexamethasone acetate or another dexamethasone derivative as well as related molecules such as beclamethasone or betamethasone. In one illustrative embodiment of the invention, the matrix comprising the compound is a matrix having the compound blended therein, for example a 60-80% silicone polymer (e.g. a biomedical grade silicone polymer) impregnated with a compound such as dexamethasone acetate.

As noted above, wide range of matrix and compound materials known in the art can be studied in the methods of the invention including metal, plastic and other polymeric matrices as well as compounds such as a steroid, an anti-coagulant an antibiotic, or an anti-inflammatory agent, for example heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopdine, a glycoprotein IIb/IIIa inhibitor or another inhibitor of surface glycoprotein receptors, or another antiplatelet agent; colchicine or another antimitotic, or another microtubule inhibitor, dimethylsulfoxide (DMSO), a retinoid or another antisecretory agent; cytochalasin or another actin inhibitor; or a remodelling inhibitor; deoxyribonucleic acid, an antisense nucleotide or another agent for molecular genetic intervention; methotrexate or another antimetabolite or antiproliferative agent; an anti-cancer chemotherapeutic agent; dexamethasone, dexamethasone sodium phosphate, dexamethasone acetate, belcomethasone (e.g. belcomethasone dipropionate) or another dexamethasone analog or derivative, or another anti-inflammatory steroid or non-steroidal antiinflammatory agent; cyclosporin or another immunosuppressive agent; trapidal (a PDGF antagonist), angiopeptin (a growth hormone antagonist), an anti-growth factor antibody, or another growth factor antagonist; dopamine, bromocriptine mesylate, pergolide mesylate or another dopamine agonist radiotherapeutic agents; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alphatocopherol, superoxide dismutase, deferoxamine, a 21-aminosteroid (lasaroid) or another free radical scavenger, iron chelator or antioxidant of any of the foregoing; or a mixture of any of these. The ratio of compound to the matrix (e.g. a therapeutic substance such as dexamethasone to a silicon polymer) will vary according to how the compound and matrix are used. A wide ratio of compound to matrix ratios can therefore be appropriate and can range from about 10:1 to about 1:100.

As discussed above, the methods of the invention can be used to study matrices impregnated and/or coated with compounds that are used or implanted in vivo including those used with pacemaker leads (e.g. in rings and tips for leads), stents, sensors, medication delivery pumps, catheters, balloons, wire guides, cannulae, and the like) and in vivo and ex vivo antimicrobial coatings and similar coatings and covers. In addition, the methods and materials of the invention can be used to assay matrices and compounds that are not implanted, such as a matrix comprising a compound that is used in industrial application, for example, compound impregnated matrices used in fermentation processes. Embodiments of the invention are adapted for observing matrices produced in batches according to one or more carefully controlled manufacturing processes (e.g. as part of a manufacturing process controlled in accordance with FDA guidelines). An exemplary embodiment of the invention involves performing the method on a plurality of matrices produced according to a uniform manufacturing process. A related embodiment of the invention involves performing the method on a plurality of such matrices made by a process designed to produce a plurality of matrices that elute the compound at the same rate. Another embodiment of this method involves further analytical steps, for example comparing the elution rates of two or more of plurality of matrices to determine if the two or more matrices have the same or different elution rates.

A wide variety of methods known in the art can be used to observe the compound in the solution including chromatographic methods such as HPLC and the like as well as immunoassays such as enzyme linked immunoadsorbent assays and the like. In view of the level of skill in this art, artisans can use any one or a wide variety of detection techniques and/or any separation technique followed by detection. Illustrative but non-limiting examples of such techniques include capillary electrophoresis, HPLC-UV; HPLC-MS (MS=Mass Spectroscopy); HPLC-UV (UPLC=Ultra performance LC) and; if for example the drug is volatile, techniques such as gas chromatography-flame ionization detection (GC/FID) in GC/FID, the FID or flame ionization detector detects analytes by measuring an electrical current generated by electrons from burning carbon particles in the sample. See, e.g. HPLC Method Development for Pharmaceuticals, Volume 8 (Separation Science and Technology), 2007 Academic Press, $1^{st}$ ed., Ahuja and Rasmussen (Editors); and Handbook of HPLC (Chromatographic Science), 1998, Marcel Dekker $1^{st}$ ed. Katz et al eds.

Related embodiments of the invention include compositions of matter: (1) made for; or (2) produced by the methods disclosed above, for example, a composition of matter comprising a solution of phosphate buffered saline having a pH range of pH 5 to pH 7; 1-9% limonene; 0.3-9% sodium dodecyl sulfate; and 0.5-15% lower alkanol. Certain specific embodiments of this composition of matter further comprise a polymer matrix impregnated with a steroid or anti-coagulant. In this context, artisans will understand that a wide variety permutations of such solutions can be readily made with minimal effort, for example phosphate buffered saline having a pH range of 5, 6 or 7 (as well as half and quarter values of these numbers such as pH 5.5 and 5.25 etc.), in combination with limonene at a concentration of 1%, 2%, 3%, 4%, 5%, 6%, 7%, 8% or 9% (as well as half and quarter values of these numbers such as 1.5% and 1.25% etc.), in combination with sodium dodecyl sulfate at a concentration of 0.3%, 1%, 2%, 3%, 4%, 5%, 6%, 7%, 8% or 9% (as well as half and quarter values of these numbers such as 1.5% and 1.25% etc.), in combination with a lower alkanol at a concentration of 0.5%, 1%, 2%, 3%, 4%, 5%, 6%, 7%, 8%, 9%, 10%, 11%, 12%, 13%, 14%, or 15% (as well as half and quarter values of these numbers such as 1.5% and 1.25% etc.). Certain specific embodiments of this composition of matter further comprise a polymer matrix impregnated with an agent designed to facilitate in vivo implantation of an apparatus such as a steroid or anti-coagulant.

An illustrative embodiment of the invention is a composition of matter comprising a solution of phosphate buffered saline having a pH range of 5-7, 3-5% limonene; 3-5% sodium dodecyl sulfate; and 3-15% lower alkanol. In certain embodiments of this composition, the lower alkanol is ethanol or n-butanol. Optionally in this composition, the solution comprises phosphate buffered saline having a pH of 6, 3-5% limonene; 3-5% sodium dodecyl sulfate; and 1-3% n-butanol.

In some embodiments of the invention, the composition of matter further comprises a matrix impregnated with an elutable agent comprising a steroid, an anti-coagulant an antibiotic, or an anti-inflammatory agent. Optionally for example, the matrix is a polymer matrix impregnated with dexamethasone acetate. In one illustrative embodiment of the invention, the composition of matter further comprises a polymer matrix is adapted for use as part of a cardiac lead.

All numbers recited in the specification and associated claims (e.g. pH 5 to pH 7; 1-9% limonene; 0.3-9% sodium dodecyl sulfate and 0.5-15% lower alkanol.) are understood to be modified by the term "about".

B. Apparatus for Inhibiting Evaporation from a Vessel

A related embodiment of the invention is an apparatus that is used, for example, to facilitate the practice of the above-noted methods by inhibiting the evaporation of dissolution media from the vessels in which elution is observed. In particular, the accuracy of quantification of a drug such as dexamethasone in dissolution/elution tests greatly depends upon maintaining the volume of the dissolution media. Evaporation is a significant issue due to the reduced amount of dissolution media used for the drug coated devices. If the volume decreases due to evaporation, it will lead to over estimation of the drug content. This is a significant issue in extended release products which are tested for a longer period of time.

Typically, the apparatus includes a cap designed to cover the vessel and inhibit dissolution media loss through evaporation. This evaporation loss cap apparatus offers easy and accurate sampling, measuring temperature and virtually no loss due to evaporation. Embodiments of the invention are useful for example in the development, production and release of drug eluting products. For example, when a product will not be approved by regulatory bodies without an appropriate elution method for studying possible process variability, the method can significantly depend upon the integrity of the cover of the vessel. In illustrative embodiments of the invention provided in the examples below, the apparatus reduces evaporation to less than 1% over a period of one week. This embodiment of the invention therefore demonstrates how dramatically the invention can reduce the evaporation of media from a dissolution vessel.

Figure 6:
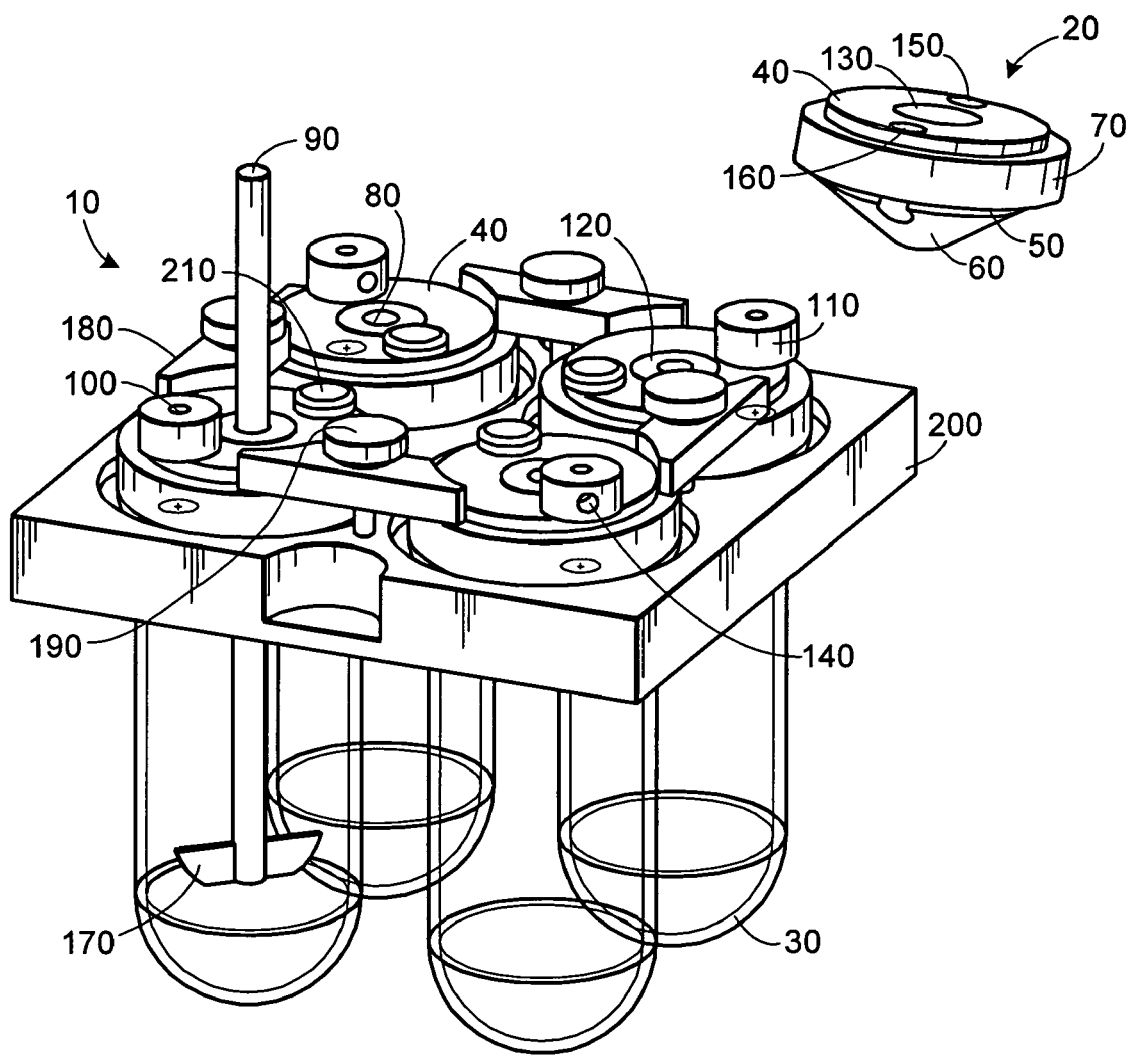
FIG. 6 shows an embodiment of an apparatus designed to inhibit fluid loss due to evaporation from a fluid dissolution vessel. This specific embodiment of the apparatus (10) comprises a cap (20) for engaging a vessel (30). The central diagram shows a group of four caps operative engaged with vessels and various interactive elements of the apparatus. The diagram at the upper right shows the cap not engaged with a vessel and/or various interactive elements of the apparatus. In the embodiment of the invention shown in this figure, the cap has a first external side (40) and a second internal side (50) that is exposed to a fluid contained in the vessel. The second side (50) comprises a conical member (60) that is designed to direct a condensate that has condensed from the fluid in the vessel onto the second side of the cap back into the fluid. The cap includes a flange (70) disposed between the first external side and the second internal side of the cap. This embodiment shows a central port (80) disposed in the cap adapted to receive a rotatable rod (90), where the material of the central port (typically Teflon) and the material of the rotatable rod are in close contact so as to create a seal that inhibits escape of a material contained within the vessel into the external environment. The rotatable rod in this embodiment includes a fluid agitation member (170) at the distal end of the rod that agitates fluid within the vessel. In this embodiment, the central port (80) is disposed in a central washer (120) that is further disposed within a central washer port (130) on the cap. This embodiment shows a sample port (100) disposed in the cap to allow a user to obtain a sample of the solution from the vessel (or to introduce a composition into the vessel) via a cannula (not shown). In this embodiment, the sample port (100) is disposed in a sample port washer (110) that is further disposed in a sample washer port (160). The sample port washer (110) further includes a cannula securing port (140) that receives a tightening screw member (not shown) that can be used to secure a cannula inserted into the sample port (100) at a desired position. This embodiment further shows a temperature member port (150) adapted to allow a user to introduce a temperature member that contacts and monitors the temperature of the solution within the vessel. The temperature member port (150) is adapted to receive a temperature port cap (210) that can cover the temperature port to inhibit escape of a material within the vessel into the external environment. All of the interacting components in this embodiment of the cap (20) are constructed to closely fit together so as to create seals that inhibits escape of a material within the vessel into the external environment. In addition, a sealing member (not shown) that contacts the vessel (30) that contains the fluid can also be disposed on the cap (20) so as to create a seal with the vessel that inhibits escape of a material within the vessel into the external environment when the cap is operatively engaged with the vessel. The embodiment of the apparatus in this figure further shows a clamp (180) that secures the cap to the vessel via a clamp screw member (190) as well as a rack (200) constructed to hold a plurality of vessels.

FIG. 6 shows a typical embodiment of an apparatus of the invention, one designed to prevent loss due to evaporation from a fluid dissolution vessel. This specific embodiment of the apparatus (10) comprises a cap (20) for engaging a vessel (30). The central diagram shows a group of four caps operative engaged with vessels and various interactive elements of the apparatus. The diagram at the upper right shows the cap not engaged with a vessel and/or various interactive elements of the apparatus. In the embodiment of the invention shown in this figure, the cap has a first external side (40) and a second internal side (50) that is exposed to a fluid contained in the vessel. The second side (50) comprises a conical member (60) that designed to direct a condensate (i.e. liquid formed by the condensation of a vapor or gas) that has condensed from the fluid in the vessel onto the second side of the cap back into the fluid. The cap includes a flange (70) disposed between the first external side and the second internal side of the cap. This embodiment shows a central port (80) disposed in the cap adapted to receive a rotatable rod (90), where the material of the central port (typically Teflon) and the material of the rotatable rod are in close contact so as to create a seal that inhibits escape of a material contained within the vessel into the external environment.

The rotatable rod in the embodiment of the invention shown in FIG. 6 includes a fluid agitation member (170) at the distal end of the rod that agitates fluid within the vessel. In this embodiment, the central port (80) is disposed in a central washer (120) that is further disposed within a central washer port (130) on the cap. This embodiment shows a sample port (100) disposed in the cap to allow a user to obtain a sample of the solution from the vessel (or to introduce a composition into the vessel) via a cannula (not shown). In this embodiment, the sample port (100) is disposed in a sample port washer (110) that is further disposed in a sample washer port (160). The sample port washer (110) further includes a cannula securing port (140) that receives a tightening screw member (not shown) that can be used to secure a cannula inserted into the sample port (100) at a desired position. This embodiment further shows a temperature member port (150) adapted to allow a user to introduce a temperature member that contacts and monitors the temperature of the solution within the vessel. The temperature member port (150) is adapted to receive a temperature port cap (210) that can cover the temperature port to prevent escape of a material within the vessel into the external environment. A sealing member (not shown) that contacts the vessel (30) that contains the fluid is typically disposed on the cap (20) so as to create a seal with the vessel that inhibits escape of a material within the vessel into the external environment when the cap is operatively engaged with the vessel. In addition, all of the interacting components in this embodiment are constructed to fit together so as to create seals that inhibit escape of a material within the vessel into the external environment so that the apparatus inhibits fluid loss from the vessel due to evaporation. This embodiment further shows a clamp (180) that secures the cap to the vessel via a clamp screw member (190) as well as a rack (200) constructed to hold a plurality of vessels.

In some embodiments of the invention, the apparatus is described as having interacting components constructed to fit together so as to create seals that prevent escape of a material within the vessel into the external environment so that the apparatus inhibits fluid loss from the vessel due to evaporation. In describing a device that "prevents escape of a material contained within the vessel into the external environment", this disclosure is intended for those of skill in this art who understand that a seal that allows the escape of one molecule (or a small number of molecules) within a vessel still prevents or essentially prevents the escape of a material contained within the vessel into the external environment. Further guidelines are provided in this regard to allow one of skill in the art to understand that prevents or essentially prevents escape of a material contained within the vessel into the external environment pertains to. These guidelines include an evaporation loss prevention cover apparatus that allows no more than 10%, preferably no more than 5%, 4%, 3% or 2% and more preferably no more than 1% of the fluid volume to escape from the vessel over a period of 3, 4 or 5, (and optionally 7) days at 25, 37 or 45 degrees centigrade.

As noted above, a typical embodiment is an apparatus for covering a vessel that contains a fluid, the apparatus comprising a cap for engaging the vessel (e.g. a circular cap), the cap having a first external side and a second internal side that is exposed to a fluid contained in the vessel, wherein the second side is cone shaped and/or comprises a conical member that facilitates deposition of a condensate from the fluid back into the fluid. Typically, a flange is disposed between the first external side and the second internal side of the cap. In some embodiments of the invention, the flange engages an edge of the vessel so as to facilitate positioning of the apparatus in an operable orientation.

In certain embodiments of the invention, the cap includes a central port disposed in the cap adapted to receive a rotatable rod that is used to stir a solution within the vessel. Optionally, the central port is disposed in a central washer that is further disposed within a central washer port on the cap. Typically, the central port comprises a teflon material (i.e. a low friction polytetrafluoroethylene polymer) disposed on a portion of the port that contacts the rotatable rod; and the portion of the central port that contacts the rotatable rod creates a seal with the rotatable rod that inhibits escape of a material contained within the vessel into the external environment. Some embodiments of the invention include an apparatus kit that includes additional elements for practicing methods of the invention such as a rotatable rod that can be disposed in the central port, wherein the rotatable rod is disposable through the central port at the portion of the conical member closest to the fluid so as to enter the portion of the vessel that contains the fluid so that the central rod acts as a fluid conduit for the condensate from the second side of the cap back into the fluid contained within the vessel. Typically, the rotatable rod includes a fluid agitation member at the distal end of the rod that agitates fluid within the vessel.

In typical embodiments of the invention, the apparatus includes a sample port disposed in the cap that is adapted to allow a user to obtain a sample of the solution from within the vessel or to introduce a composition into the vessel. Optionally, the sample port is disposed in a sample port washer that is further disposed within a sample washer port on the cap (e.g. as shown in FIG. 6). In one embodiment of the invention, the sample port washer is disposed on the cap to guide and support a cannula that contacts the solution within the vessel. Typically, portions of the sample port washer that contact the cannula and the portions of the sample port washer that contacts the sample washer port create seals that inhibits escape of a material contained within the vessel into the external environment.

In some embodiments of the invention, the sample port is adapted to allow a user to introduce a temperature member (e.g. a thermometer, thermocouple or the like) that contacts and monitors the temperature of the solution within the vessel. In other embodiments of the invention, the apparatus further comprises a distinct temperature member port in the cap that is adapted to allow a user to introduce a temperature member that monitors the temperature of the solution within the vessel and is also adapted to receive a temperature member port cap that covers the temperature member port to inhibit escape of a material within the vessel into the external environment.

Typical embodiments of the invention include a sealing member disposed on the cap that contacts the vessel that contains the fluid so as to create a seal with the vessel that inhibits escape of a material within the vessel into the external environment when the cap is operatively engaged with the vessel. In some embodiments of the invention, the sealing member is coupled to, adjacent to or supported by the flange. A variety of sealing members and mechanisms known in the art can be used as a sealing member. In certain embodiments of the invention, the sealing member is an O-ring. In some embodiments of the invention, the cap includes a groove or indentation for securing the sealing member.

In certain embodiments of the invention, a portion of the apparatus that contacts fluid in the vessel (e.g. fluid condensate) is comprised of a material that is resistant to degradation by a solution comprising: phosphate buffered saline at pH range of pH 5 to pH 7; 1-9% limonene; 0.3-9% sodium dodecyl sulfate and 0.5-15% lower alkanol. In some embodiments of the invention this portion is made of Delrin. Similarly, in some embodiments of the invention, the O-ring is made of Viton The apparatus can include a variety of other elements that facilitate methods of observing elution of a compound from a composition. For example, certain embodiments of the apparatus can include one or more clamps that secure the cap to the vessel. Other embodiments of the invention include a sampling member adapted to allow a user to obtain a sample of the solution from within the vessel or to introduce a sample into the vessel, wherein the sampling member comprises an angled cannula adapted to obtain multiple fluid samples from the same location within the vessel. In such embodiments of the invention, the angle of the angled cannula adapted serves as a physical barrier to cannula movement and directs the cannula to the same place within the vessel over and over again so as to maintain consistency of sample collection. In addition, some embodiments of the invention include a rack to hold a plurality of capped vessels.

Typically, the components of the apparatus (e.g. the washers and washer ports) are designed to fit together so as to create seals that prevent escape of a material within the vessel into the external environment so that the apparatus inhibits fluid loss from the vessel due to evaporation. Moreover, all portions of the apparatus that allow access to the fluid within the vessel (e.g. the central and sample ports) can be adapted to receive a cap member that covers the port so as to inhibit escape of a material within the vessel into the external environment. In addition, in typical embodiments of the invention, the cap is of unitary construction, meaning that its material is made from a single cast of material and has no seams or joints that provide avenues for fluid loss. In an exemplary embodiment of the invention, the apparatus reduces fluid loss due to evaporation to less than 5%, 4%, 3%, 2% or 1% of the fluid contained within the vessel over 7 days at 37 degrees centigrade. In another exemplary embodiment of the invention, the apparatus reduces fluid loss due to evaporation to less than 5%, 4%, 3%, 2% or 1% of the fluid contained within the vessel over 15 days at 37 degrees centigrade.

The apparatus disclosed above can be modified in order to adapt it for use in a wide variety of contexts. In some embodiments of the invention, the sampling port can also act as a temperature measuring port by enabling the introduction of a thermo-couple into the vessel for temperature measurements. In other embodiments, it has a separate port which acts as a temperature port. In some embodiments of the invention, a sampling cannula is introduced using the sampling port such that the point of sampling inside the vessel can be easily adjusted. The sample introduction port provides a correct and an easy way of introducing the sample into the dissolution vessel and significantly increases the accuracy of the sampling and also the precision of sampling. In addition, this apparatus can be used to sample manually or can be adapted for use with an automatic sampler. A number of further embodiments of the invention will be readily apparent to those of skill in the art, including for example, elution methods of the invention that are practiced using the apparatus of the invention as well as methods of making the apparatus according to art accepted techniques.

The methods and apparatuses disclosed herein can be adapted for use in a wide variety of procedures known in the art. All patent and literature references (e.g. Shah et al., International Journal of Pharmaceutics 125 (1995) 99-106; AAPS PharmSci 2002; 4 (2) article 7; AAPS PharmSci 2004; 6 (1) Article 11; Guidance for Industry, Extended Release Oral Dosage Forms: Development, Evaluation, and Application of In Vitro/In Vivo Correlations, U.S. Department of Health and Human Services Food and Drug Administration Center for Drug Evaluation and Research (CDER), September 1997, BP 2; Palamakula et al., Preparation and In Vitro Characterization of Self-Nanoemulsified Drug Delivery Systems of Coenzyme Q10 Using Chiral Essential Oil Components, Pharmaceutical Technology OCTOBER 2004; Lawrence et al., Advanced Drug Delivery Reviews 45 (2000) 89-121 and U.S. Pat. Nos. 6,063,314; 4,819,662; 5,464,650; 5,609,629; 20040037886; and 20030208236) are incorporated by reference herein.

Embodiments of the invention include kits comprising a first container, a label on said container, and a composition contained within said container. Such kits include elution media components in one or more containers having a label, the label on said container, or a package insert included in said container indicates that the composition can be used to elute a composition form a matrix. Optionally the kit includes a premixed, ready to use elution media. Optionally the kit includes additional elements such as an apparatus for using the media, an embodiment of which is shown in FIG. 6. Other embodiments of the invention include a kit containing an apparatus for using the media, an embodiment of which is shown in FIG. 6, in the absence of elution media components.

EXAMPLES

Example I

Determination of Elution (In-Vitro Dissolution) of Dexamethasone Acetate Impregnated Product Typical Methods and Materials Used to Practice the Invention
Typical Chemicals:
(R)-(+)-Limonene, 97% (or above), Sigma-Aldrich Catalog #: 183164500ML, or equivalent
Sodium Phosphate Monobasic (NaH2PO4), Sigma Catalog Number S8282, or equivalent
Sodium Phosphate Dibasic (Na2HPO4), Sigma Catalog Number S7907, or equivalent Sodium Chloride
Sodium Dodecyl Sulfate (Sigma Catalog #L6026 or equivalent)
Acetonitrile, HPLC grade
1 N Sodium Hydroxide Solution
Process Water
USP Dexamethasone Acetate Reference Standard
Ammonium formate, Fluka Catalog #17843 or equivalent
Formic Acid, Fluka Catalog #06450 or equivalent
Sodium Hydroxide, Reagent Grade
Hydrochloric Acid, Reagent Grade
Potassium Chloride
Potassium Phosphate, Monobasic
1-Butanol Typical Preparation of 0.5 M Potassium Phosphate Monobasic Solution
  Weigh 6.8 grams of potassium phosphate monobasic into a 100 mL volumetric flask. Dilute with process water to volume, and mix.

Typical Preparation of pH 6.0 Buffer Solution
  Transfer 3.0 mL of 1N sodium hydroxide solution, 138 mL of 0.5 N potassium chloride solution, and 50 mL of 0.5 M potassium phosphate monobasic solution to a 1-L volumetric flask, dilute with process water to volume, and mix.

Typical Preparation of Standard Diluent
  Mix 500 mL of acetonitrile and 500 mL of pH 6.0 Buffet solution (1:1) to obtain 1-L standard diluent.

Typical Preparation of Media:
  Preparation of 0.05M Phosphate Buffered Saline (PBS) Solution, pH 6.0:
    This procedure is for preparing 4 L of 0.05M phosphate buffered saline (PBS). Other volumes of the PBS solution can be prepared by appropriately scaling down or scaling up the quantities of the materials.
  Weigh carefully 36±1.8 grams of Sodium Chloride into a 4 Liter graduated cylinder.
  Add 3 L of process water to the cylinder.
  Stir until completely dissolved.
  Weigh carefully 22.8±1.1 grams of Sodium Phosphate Dibasic and add to the same cylinder
  Stir until completely dissolved
  Weigh carefully 4.4±0.2 grams of Sodium Phosphate Monobasic and add to the same cylinder.
  Stir until completely dissolved
  Adjust the pH of the solution to 6.0±0.1 using 1N Hydrochloric Acid to reduce the pH. If necessary use 1N Sodium Hydroxide to increase the pH.
  After adjusting the pH dilute with process water to 4 L volume.
  Transfer the solution to an appropriate bottle and label it as PBS Media, pH 6.

Typical Preparation of Four Liters of 5% (w/w) (R)-(+)-Limonene Media with 5% Sodium Dodecyl Sulfate and 2% 1-Butanol (Elution Media):
  This procedure is for preparing 4 L of the media. Other volumes can be prepared by changing the quantities of the materials appropriately.
  Weigh carefully 200.0±2 grams of sodium dodecyl sulfate (SDS) into a 5 L beaker.
  Weigh carefully 200.0±6 grams of (R)-(+)-Limonene and transfer it into the same beaker. Mix. Add 80.0±2 grams of 1-Butanol and then mix.
  Weigh carefully 3520 g±192 g of PBS Media, pH 6 and add slowly to the same beaker.
  Mix contents thoroughly using a hotplate stirrer and stir bar.
  Transfer the solution to a 5 L glass bottle and label appropriately.

Typical Standard Preparation
  Weigh 100 mg Dexamethasone Acetate Reference Standard into a drying dish and dry under vacuum in a vacuum oven at 105° C. for 3 hours. (Dried powder should can stored in a desiccator and used up to 7 days). Prepare a standard solution of 100 μg/mL of dexamethasone acetate in Standard Diluent.

Elution Procedure

Typical Dissolution System Setup
  Attach the low loss evaporation covers to the mini paddle and mount the mini paddles to the drive unit. Attach the cannulas to the low loss evaporation covers.
  Lower the drive unit holding the paddles and set the paddle heights at 25 mm, the distance between the blade of the paddle and the inside bottom of the vessel, using the 25 mm ball or any appropriate gauge. This distance is maintained during the test.
  Add 75 mL of Elution Media to each mini vessel.
  Hold the low loss evaporation covers in place using the clamps.
  Adjust the cannula position such that the cannulas do not touch/interfere with each other. Adjust the cannula by either raising or lowering it such that the position of the cannula is approximately midway between the top of the paddle and the surface of the Elution Medium. Use the plastic screw on the probe that hosts the cannula to tighten and maintain the position of the cannula.

Seal the outer end of the cannulas (positioned outside the mini vessel) using appropriate plugs or empty syringes or parafilm. If this end is not sealed, it might lead to the loss of the media through evaporation.

Allow the Elution Media to equilibrate to 45±0.5° C.

Measure and record the temperature of the media in all of the vessels.

Set the elution parameters according to Table 1A:

TABLE 1A

Typical Elution Parameters

| Parameter | Specification |
|---|---|
| Apparatus | USP Apparatus 2 with mini vessels, mini paddles, covered by low evaporation loss covers |
| Media Information | 5% R-(+)-Limonene, 5% SDS, 2% Butanol in PBS Buffer, pH 6.0 |
| Media Volume | 75 ml |
| Media Temperature: | 45.0 ± 0.5° C. |
| Media withdrawn/replaced | 1 ml |
| Shaft Speed | 100 rpm |
| Evaporation Control | Special low evaporation loss covers |
| Typical Time Points* | 6 hr, 12 hr, Day 1, Day 2, Day 3, Day 4, Day 6, Day 8, Day 10, Day 12 |

Disengage the clamps that are holding the low loss evaporation covers.

Raise the drive unit carefully.

Carefully drop each sample into a separate individual vessel. Make sure the samples reach the bottom of the vessel.

Lower the drive unit into place. Secure the drive unit in place.

Ensure that the low loss evaporation covers are covering the mini vessels.

Immediately start rotating the paddle by using the menu on the dissolution vessel and simultaneously start the timer.

Secure the low loss evaporation covers using the clamps.

At the sampling time points, remove the seal from the cannula.

Use a 1 to 3 mL syringe to remove 1 mL of sample. Transfer the sample into a HPLC vial of 2 mL capacity. Close the vial using an appropriate lid. Each vessel will have a dedicated syringe and cannula.

Take 1 mL of fresh Elution Media in a clean, new syringe and transfer it slowly into the mini vessel using the cannula.

Seal the outer end of the cannulas (positioned outside the mini vessel) using appropriate plugs or empty syringes or parafilm Repeat Steps for each sample.

Analyze the pulled samples using chromatographic analysis such as HPLC.

As an illustrative embodiment of the invention, a drug dissolution method (in-vitro) was developed for the elution of Dexamethasone Acetate (Dexamethasone Acetate) from a typical CRD product (CRD=Controlled Release Device). A variety of CRD products are known in the art, and include for example tips and rings used with electronic leads (see, e.g. U.S. Pat. Nos. 5,987,746, 6,567,704, and 7,184,839 and U.S. Patent Application 20020138123, the contents of which are incorporated by reference). The method is required to support product development, quality control of the product and meet regulatory requirements (see, e.g. FDA Guidance for Industry (CDRH), "Guidance for the Submission of Research and Marketing Applications for Permanent Pacemaker Leads and for Pacemaker Lead Adaptor 510 (k) Submissions", November 2000; and Burgess et al., "Critical Quality and Performance Parameters for Modified-Release Parenteral Dosage Forms", Pharmacopeial Forum, 2005, 31 (6), p. 1745).

Method Development

The steps in method development included adaptations of methods and materials known in the art, for example USP General Chapter <1092>, In-Process Revision, "The Dissolution Procedure: Development and Validation", Pharmacopeial Forum, 2005, 31 (5), p. 1463; Burgess et al., "Assuring Quality and Performance of Sustained and Controlled Release Parenterals: Workshop Report", AAPS PharmSci, 2002, 4(2), article 7; and Burgess et al., "Assuring Quality and Performance of Sustained and Controlled Release Parenterals: EUFEPS Workshop Report", AAPS PharmSci, 2004, 6(1), article 11. The development of the method included:

Preparation of Device for Elution Studies

Choice of Elution Parameters—effect of pH on solubility of drug, choice of media & additives, volume of media Evaluation of sink condition Choice of apparatus along with its parameters Choice of analytical method—for detection and quantification, sampling points Elution discrimination studies A first step was to determine the solubility of the product using standard aqueous dissolution media, several of which are listed in the USP (see, e.g. USP General Chapter <724>, "Drug Release"), literature (see, e.g. Noory et. al., (Food and Drug Administration—CDER), "Steps for Development of a Dissolution Test for Sparingly Water-soluble Drug Products", Dissolution Technologies, 2000, 7(1), Article 3) and the US FDA website (see, e.g. FDA website link for dissolution medias using search terms: "accessdata.fda.gov/scripts/cder/dissolution/"). The initial run can allow evaluation of the effect of pH on the product. If the product exhibited poor dissolution, then the need for a surfactant (below the critical micelle concentration forming emulsions) can be evaluated.

Dexamethasone acetate is a steroid, sparingly soluble in water. Dexamethasone Acetate is distributed in the polymer matrix as dispersion. The drug generally diffuses from the matrix into the fluidic system where the lead is placed. In typical embodiments of the invention, it is important to use a dissolution medium that exhibits good thermodynamic compatibility with the polymer (see, e.g. Peppas et al., "Modeling of Drug Diffusion through Swellable Polymeric Systems", Journal of Membrane Science, 1980, 7, p. 241-253; and Paul, D. R., "Controlled Release Polymeric Formulations", ACS Symposium Series, volume 33, ACS, Washington, 1976). A dissolution medium comprised of a surfactant forming emulsion (macro, micro or nano) would offer such thermodynamic stability with the polymer. Use of surfactant is physiologically relevant and can be successfully used for dissolution testing.

A literature survey showed that the elution of dexamethasone-eluting cardiac pacing electrodes is less than 19% in 24 days if PBS (without additives) is used (see, e.g. Casas-Bejar et. al., "Medical Electrical Leads and in-dwelling Catheters with enhanced Biocompatibility and Biostability", United States Patent Publication, Publication #US 20020138123 A1, Application Number 998536, Sep. 26, 2002) (PBS=Phosphate Buffered Saline). Another study conducted by Guidant Corporation, showed elution at about 10% in 30 days (see, e.g. Heil, R (Guidant Corporation), "In Vivo Comparison of Dexamethasone-eluting cardiac pacing electrode technologies with different release rates", Proceed. Int'l. Symp. Control. Rel. Bioact. Mater., 2000, 27, p. 471). The percent elution was less than 7% in 10 days from the CRD leads when PBS (pH 5) without any additives was used. The information indicates that though the drug may be soluble in the buffered media at low concentrations (see sink condition evaluation below), the drug dissolution will be controlled by diffusion from the polymer.

Preparation of Device for Elution Studies

The drug eluting portion of samples were cut separately from the device and used for the purpose of testing. The CRD section was cut from the device such that the length of the section was approximately 1-2 cm.

Choice of Elution Parameters

To evaluate buffers with different pH, eleven milligrams of Dexamethasone Acetate was dissolved in 500 mL of media (different pH adjusted buffers). The stability of Dexamethasone Acetate with respect to pH followed this order: pH 3>pH 5≅acetate pH 5.7>water>pH 7>pH 9. This concentration was about 10 times the concentration that might be observed if the drug from the typical device was completely eluted in about 75 mL of media. This confirmed that the sink condition was appropriate in the buffers above.

The next steps involved attempting to increase the elution by adding different types of additives, capable of forming macro-emulsions, to the media. This was in concurrence with the USP, US FDA and industry guidelines for performing elution on a sparingly soluble drug substance (see, e.g. USP General Chapter <1092>, "The Dissolution Procedure: Development and Validation", Pharmacopeial Forum, 2005, 31 (5), p. 1463; FDA Guidance for Industry (CDER), "Extended Release Oral Dosage Forms: Development, Evaluation and Application of In Vitro/In Vivo Correlations", September 1997; FDA Guidance for Industry (CDER), "Immediate Release Solid Oral Dosage Forms Scale-Up and Postapproval Changes: Chemistry, Manufacturing, and Controls, In Vitro Dissolution Testing, and In Vivo Bioequivalence Documentation", November 1995; 4. Burgess et al. "Assuring Quality and Performance of Sustained and Controlled Release Parenterals: Workshop Report", AAPS PharmSci, 2002, 4(2), article 7; Burgess et al., "Assuring Quality and Performance of Sustained and Controlled Release Parenterals: EUFEPS Workshop Report", AAPS PharmSci, 2004, 6(1), article 11, respectively). The suitability of different classes of surfactants, namely, anionic (e.g. sodium dodecyl sulfate), cationic (e.g. Cetyl trimethyl ammonium bromide—CTAB) and non-ionic (e.g. Solutol HS 15-poly-oxyethylene esters of 12-hydroxystearic acid, Tween 80) as an additive to the elution media was evaluated. There was no significant increase in elution of Dexamethasone Acetate from the CRD. The maximum elution obtained was about 13% in 26 days in a media with the addition of 5% Solutol.

Since the surfactants did not increase the elution of Dexamethasone Acetate significantly, a two-tier elution method involving a co-surfactant was attempted. This followed a model similar to that used in gelatin capsules (see, e.g. FDA website link for dissolution medias using search terms: "accessdata.fda.gov/scripts/cder/dissolution/") (Dutasteride Soft Gelatin Capsule) and USP elution methods. However, due to the two-tier nature of the media, this media evaluation was discontinued.

In an effort to develop an accelerated elution method that would better penetrate the polymer matrix and that would increase diffusion (instead of surface elution), media with additives that form a micro-emulsion or nano-emulsion were evaluated. The evaluations determined that Limonene, along with sodium dodecyl sulfate, provided a emulsion media that is thermodynamically stable (see e.g., Palamakula et al., "Preparation and In-Vitro Characterization of Self-nanoemulsified Drug Delivery Systems of Coenzyme Q10 using Chiral Essential Oil Components", Pharmaceutical Technology, 2004, 28(10), 74-88).

Micro-emulsions are widely used in drug delivery systems (see, e.g. Lawrence, M. J., Rees, G. D., "Micro-emulsion based Media as Novel Drug Delivery Systems", Advanced Drug Delivery Reviews 45, 2000, p. 89-121). Advantages associated with micro-emulsions include their thermodynamic stability and ease of preparation. The existence of micro domains of different polarity within the same single-phase solution enables both water-soluble and oil-soluble materials to be solubilized, at the same time if desired. It should be noted that the solubilisate partitions between the micro-emulsion droplet and continuous phase and that while there may be a preferred site of solubilisation within the micro-emulsion droplet, the solubilisate may be located at one of a number of sites. For example, the likely preferred sites of incorporation of a lipophilic, water-insoluble drug into an oil/water micro-emulsion are the disperse oil phase and/or hydrophobic tail region of the surfactant molecule, while a water-soluble material would be most likely to be incorporated into the dispersed aqueous phase of a water-in-oil droplet. The attraction of micro-emulsion systems lies in their ability to incorporate hydrophobic drugs into the apolar oil phase thereby enhancing their solubility (see, e.g. Paul, D. R., "Controlled Release Polymeric Formulations", ACS Symposium Series, volume 33, ACS, Washington, 1976).

The effect of media containing different concentrations of limonene and sodium dodecyl sulfate was studied. The media comprised of 3% Limonene and 1% SDS in pH 6 PBS was found to be optimal for the elution of the typical device. The media was able to accelerate the elution rate. For example, elution of Dexamethasone Acetate from CRD 2 was about ~100% in 8 days while it was more than 70% for the CRD 1 in 15 days. The media was also able to discriminate nominal lots from a process variation lot; (see sections below for the elution data of nominal and process variation lots and the discrimination data). The elution plots were representative of those observed with non-disintegrating type products (see, e.g. Hanson, R., Gray, V., Handbook of Dissolution Testing, Page. 22, $3^{rd}$ Edition, Dissolution Technologies, Inc, Hockessin, Del.). In an effort to enhance drug elution in stronger or higher crosslinked matrix, or to accelerate elution, media with components that provide more thermodynamic stability (i.e. a form of a nano-emulsion) was developed. One typical media comprised 5% R-(+)-Limonene, 5% SDS and 2% 1-Butanol in pH 6 PBS.

Evaluation of Sink Conditions

The media (5% R-(+)-Limonene, 5% SDS and 2% 1-Butanol in pH 6 PBS) was found to meet the sink conditions, as outlined in elution method development guidelines. This sink condition study proved that the drug was fully soluble even at ten times the sample concentration expected when the drug in the typical device is completely dissolved in 75 mL media.

Choice of Apparatus

The apparatus chosen for this method was USP Apparatus 2 (Paddles). During method development, it was found the elution rate was slightly higher in the Apparatus 2 than the Apparatus 1 (Basket). Due to the low content of the drug in the device, mini vessels with mini paddles were chosen for the method. The apparatus was set at 100 rpm. A media volume of 75 mL was found appropriate for the analytical methods detection capability and met the sink conditions. The media was maintained at 45° C.±0.5° C. The sample pull volume was 1 mL at each time point with media compensation, in line with elution guidelines.

Choice of Analytical Method of Quantification of Dexamethasone Acetate

The initial choice of analytical method was UV-Vis. However, due to the low concentration of drug present in the material, HPLC with UV detection was found to be the method of choice.

The mobile phase preparation and choice of the column were instructed in the Dexamethasone Acetate monograph USP29-NF24. The mobile phase A consisted of pH 4.1 formate buffer and acetonitrile (3:2), and mobile phase B consisted of pH 4.1 formate buffer and acetonitrile (9:1). The chromatographic column (USP L11) used was an Agilent Zorbax SB-Phenyl, 4.6 mm×250 mm, 5 µm. A gradient was used with 1 mL/min flow rate. The run time was about 70 minutes. The UV detection wavelength was 262 nm, where the method was found to be specific for quantification of Dexamethasone Acetate in the elution medium. The injection volume for standard and samples was 100 µL. The drug was found to be stable in the media for the length of the study.

Sampling Time Points and Elution Data

Figure 1B:
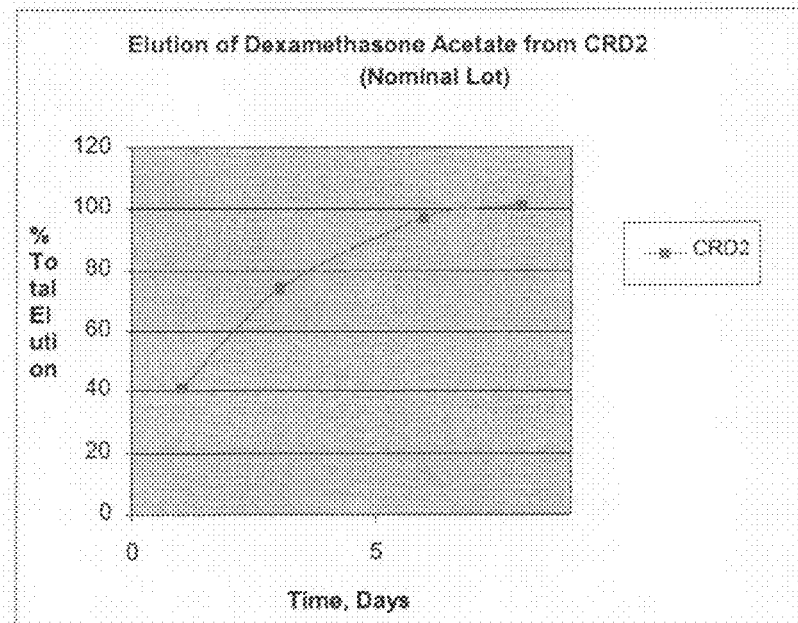

The elution of Dexamethasone Acetate from CRD from a nominal lot is compared and presented in FIGS. 1A and 1B which show a typical plot of elution of dexamethasone acetate from CRDs.

The elution pattern for CRD were similar to the profile of a non-disintegrating product (see, e.g. Hanson, R., Gray, V., Handbook of Dissolution Testing, Page. 22, 3$^{rd}$ Edition, Dissolution Technologies, Inc, Hockessin, Del.). This profile was generally obtained where the dissolution rate was determined by the process of diffusion and dissolution.

Figure 2:
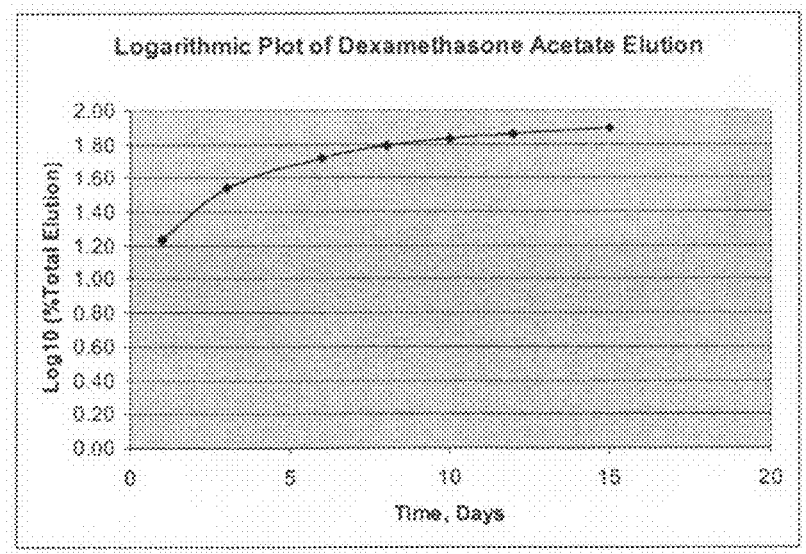
FIG. 2 shows a logarithmic plot of drug elution in Device 1.

The logarithmic plot of elution of Dexamethasone Acetate versus Time (See FIG. 2 which shows logarithmic plot of drug elution in CRD 1) shows that the elution rate had essentially reached a plateau (asymptote) at 8 days. The optimal sampling time points were chosen as 1, 3, 6 and 8 days for the typical CRD.

Figure 3:
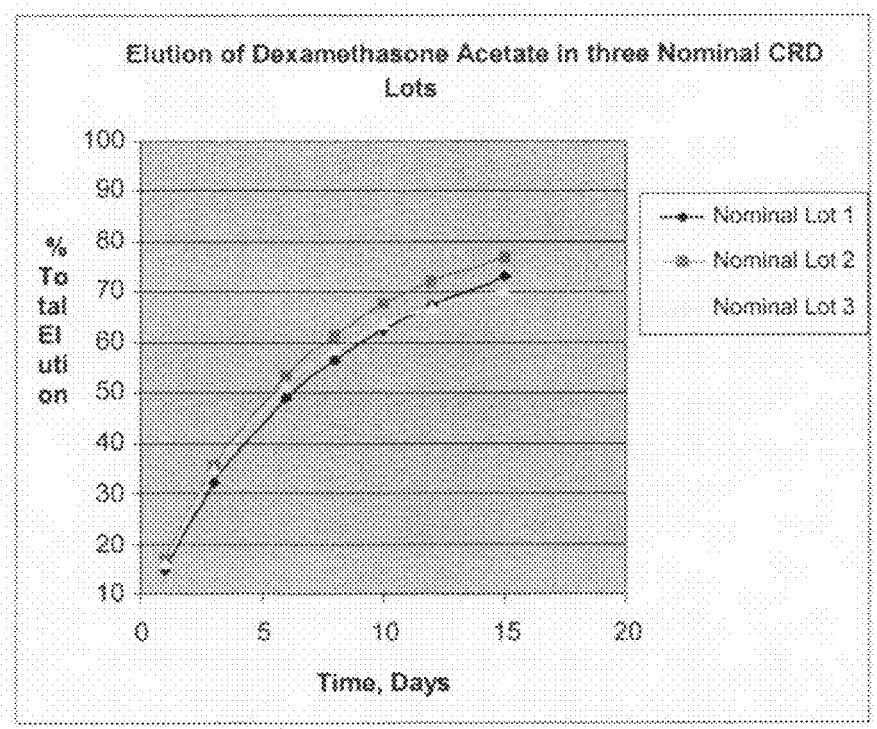
FIG. 3 shows dexamethasone elution data from three different lots of CRD 1 (nominal process).

Three different nominal lots of the typical CRD were analyzed using the recommended elution method proposed. The results are presented in FIG. 3. The results show the similarity in elution profile among the three different nominal lots of the device.

Elution Discrimination Studies

The discriminating nature of the elution method was studied by testing three lots of the same device. One lot was manufactured using the nominal process and each of the other two lots was manufactured with different process variations. The elution method was capable of discriminating between the nominal and process variation lots.

In the first study, using 6 samples from each lot, the elution of Dexamethasone Acetate from CRD 1 was about 77% in 15 days for the nominal lot, while the elution was about 56% in 15 days for the lot with first process variation. For the CRD 2, the elution of Dexamethasone Acetate was about 101% in 8 days for the nominal lot while the elution was about 84% in 8 days for the process variation lot. The results also met the criteria for discrimination for the similarity factor, F2, as specified in the US FDA guidelines. For the CRD 1 and 2, the F2 values (see calculation formula below) were 41 and 45 respectively.

Figure 4:
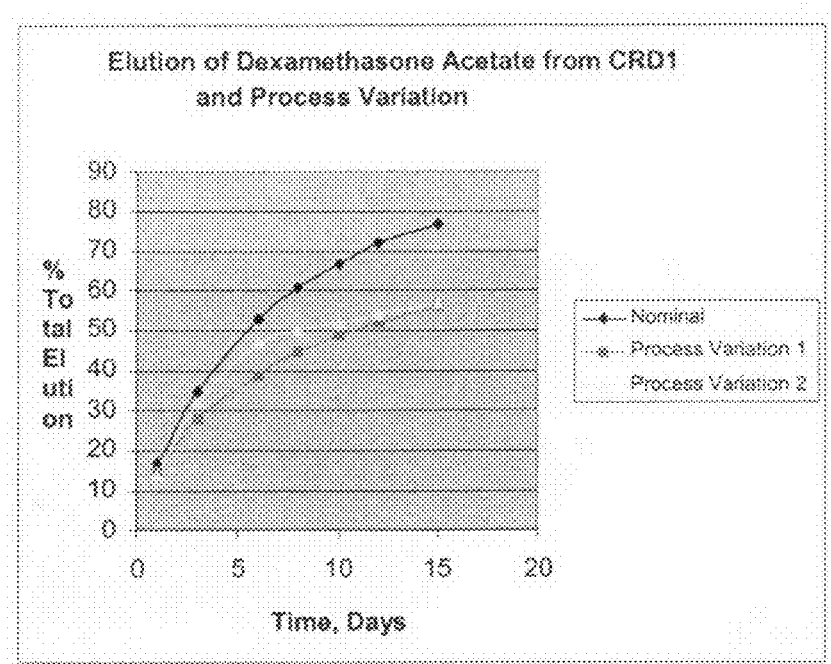
FIG. 4 shows a discriminatory study of the elution of dexamethasone acetate from CRD 1.
Figure 5:
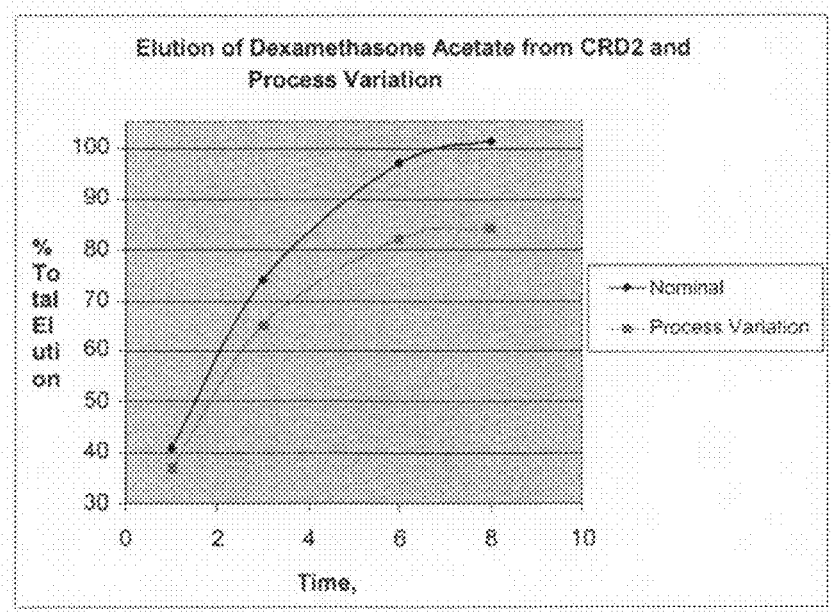
FIG. 5 shows a discriminatory study of the elution of dexamethasone acetate from a second CRD.

In the second study, the results obtained for the CRD 1 Samples from the nominal lot were compared with that of a second process variation lot. Six samples from each lot were used. Elution of Dexamethasone Acetate from CRD 1 was 77% in 15 days for the nominal lot while the elution was about 57% in 15 days for the second process variation lot. The results also met the criteria for discrimination for the similarity factor, F2, as specified in the US FDA guideline (see, e.g. FDA Guidance for Industry (CDER), "Extended Release Oral Dosage Forms: Development, Evaluation and Application of In Vitro/In Vivo Correlations", September 1997; and FDA Guidance for Industry (CDER), "Immediate Release Solid Oral Dosage Forms: Scale-Up and Postapproval Changes: Chemistry, Manufacturing, and Controls, In Vitro Dissolution Testing, and In Vivo Bioequivalence Documentation", November 1995). The calculated F2 value was 45. The elution data obtained during discriminating studies are presented in FIGS. 4 and 5.

Figure 7A:
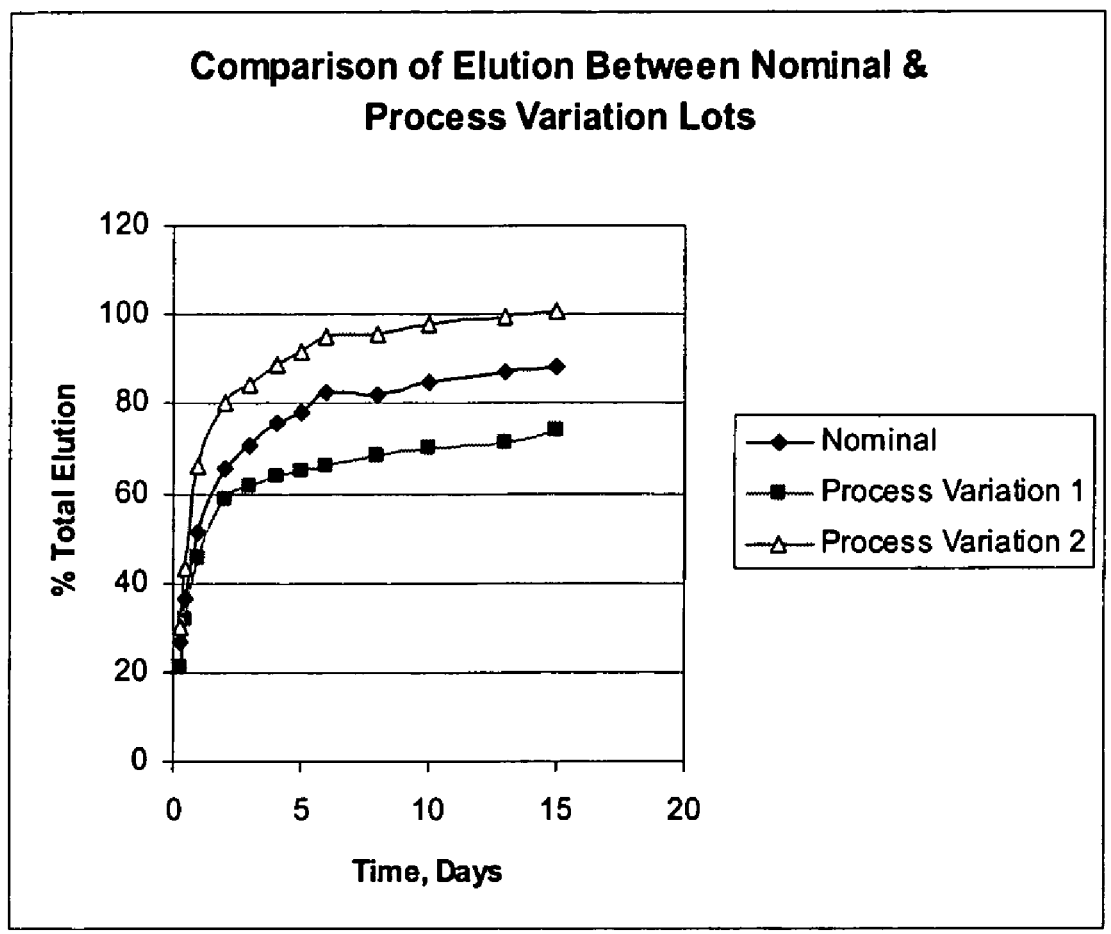
FIG. 7A provides a graph showing a comparison of elution profiles of a steroid from drug eluting lead components over about 15 days using a media embodiment of the invention comprising 5% R(+) Limonene, 5% SDS, and 2% n-butanol in PBS pH 6. This graph provides a discriminatory study with the drug impregnated matrix made according to the Nominal process as well as Process Variation 1 and Process Variation 2.

In a third study, using the media described in Table 1A, CRD 1 was subjected to elution studies; the F2 values were 47 and 44 respectively for two process variations. The elution data obtained during discriminating studies are presented in FIG. 7A.

Figure 7B:
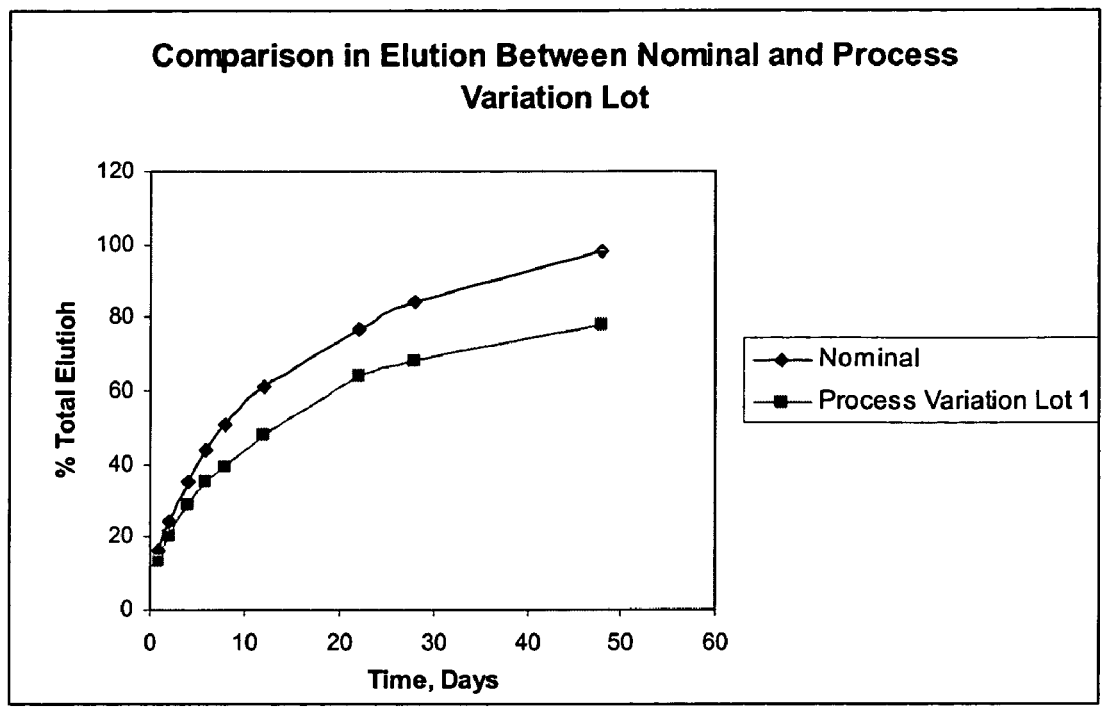
FIG. 7B provides a graph showing a comparison elution profiles of a steroid from drug eluting leads over about 50 days using a media embodiment of the invention comprising 5% R(+) Limonene, 5% SDS, and 2% n-butanol in PBS pH 6. This graph provides a discriminatory study with the drug impregnated matrix made according to the nominal process as well as process variation 1.

In a fourth study, using the media described in Table 1A, CRD 2 was subjected to elution studies; the F2 value was 46 for the process variation. The elution data obtained during discriminating studies are presented in FIG. 7B As per the elution guidelines the F2 factor should be less than 50 to consider the method to be discriminating (see, e.g. FDA Guidance for Industry (CDER), "Extended Release Oral Dosage Forms: Development, Evaluation and Application of In Vitro/In Vivo Correlations", September 1997; and FDA Guidance for Industry (CDER), "Immediate Release Solid Oral Dosage Forms: Scale-Up and Postapproval Changes: Chemistry, Manufacturing, and Controls, In Vitro Dissolution Testing, and In Vivo Bioequivalence Documentation", November 1995). The F2 results calculated above demonstrate that the method is discriminating.

Formula for F2 Calculation:

$$F2 = 50 \ LOG\{[1+1/n\Sigma^{n}_{t=1}(R_t-T_t)^2]^{-0.5} \times 100\}$$

Where $R_t$ and $T_t$ are the percent dissolved at each time point]

Conclusion

The in-vitro dissolution method summarized below was found to be suitable for testing drug elution from steroid eluting products such as leads. The elution media was found to be discriminating between the nominal samples and samples that were manufactured with process variations. The details of the elution method are summarized in Table 1B below:

TABLE 1B

Typical Second Elution method
Summary of Method
Elution of Dexamethasone Acetate from Steroid Eluting Products

| Apparatus | Modified USP Apparatus 2 with mini-vessels and mini-paddles |
|---|---|
| Elution Media | 3% R-(+)-Limonene and 1% SDS in pH 6 PBS |
| Media Volume | 75 mL |
| Paddle Speed | 100 RPM |
| Water Bath Temperature | 37.0° C. ± 0.5° C. |
| Sampling Time Points | Days 1, 3, 6 and 8 |
| Sample Volume | 1 mL with media replacement |

Example 2

Media Embodiments Comprising a Lower Alkanol Cosolvent

Embodiments of the invention include elution media comprising a cosolvent in the form of a lower alkanol and methods for using this media. A typical media embodiment having a cosolvent includes for example 5% R (+) Limonene, 5% Sodium Dodecyl Sulfate, 2% n-Butanol in PBS pH 6.0. This media embodiment was used in the studies shown in FIGS. 7B and 7C. While this is a typical recipe, media embodiments of the invention can include a wide variety of concentration ranges for the various constituents in the media composition, for example those included in TABLE 1C below.

TABLE 1C

| % R (+) Limonene | % SDS | % Alcohol |
|---|---|---|
| 7 | 5 | 0.5 - Butanol |
| 3 | 1 | 0.5 - Butanol |
| 3 | 1 | 2 - Butanol |
| 5 | 5 | 2 - Butanol |
| 3 | 1 | 5 - Butanol |
| 5 | 5 | 5 - Ethyl alcohol |
| 2 | 1 | 0 |
| 3 | 1 | 0 |
| 4 | 2 | 0 |
| 5 | 2 | 0 |
| 5 | 5 | 0 |
| 6 | 3 | 0 |
| 7 | 1 | 0 |
| 7 | 2 | 0 |
| 7 | 5 | 0 |
| 8 | 8 | 0 |
| 5 | 7 | 0 |
| 3 | 7 | 0 |
| 1% R (+) Limonene + 1% S (−) Limonene | 1 | 0 |

Those of skill in the art can readily make such media compositions using commercially available reagents. In one illustrative embodiment for example comprising 100 ml of a media composition comprising 5% R (+) Limonene, 5% Sodium Dodecyl Sulfate, and 5% n-Butanol in PBS, 5% value reflects the value of the total constituent (e.g. 5 grams of alcohol+5 grams of limonene+5 grams of SDS+85 grams of PBS solution).

Typical conditions and/or methodological steps (e.g. temperature, agitation etc.) that can be used with this cosolvent media are included in TABLE 1A above.

All patent and literature references cited in the present specification are hereby incorporated by reference in their entirety.

The invention claimed is:

1. A method for observing the elution of a compound from a matrix comprising the compound into a solution, the method comprising exposing the matrix comprising the compound to a solution, wherein the solution comprises:
   phosphate buffered saline having a pH range of pH 5 to pH 7;
   1-9% limonene;
   0.3-9% sodium dodecyl sulfate; and
   0.5-15% lower alkanol; and
assaying the solution for the presence of the compound so as to observe the elution of the compound from the matrix into the solution.

2. The method of claim 1, wherein the lower alkanol is ethanol or n-butanol.

3. The method of claim 1, wherein the solution comprises:
   phosphate buffered saline having a pH of 6;
   3-5% limonene;
   3-5% sodium dodecyl sulfate; and
   1-3% n-butanol.

4. The method of claim 1, further comprising performing the method on a plurality of matrices made by a process designed to produce a plurality of matrices that elute the compound at the same rate and comparing the elution rates of two or more of plurality of matrices to determine if the two or more matrices have the same or different elution rates.

5. The method of claim 1, wherein the solution is assayed for the presence of the compound using high performance liquid chromatography (HPLC).

6. The method of claim 5, wherein the matrix comprising the compound is a polymer matrix having the compound blended therein.

7. The method of claim 6, wherein the matrix comprises a biomedical grade silicone polymer.

8. The method of claim 1, wherein the compound comprises a steroid, an anti-coagulant an antibiotic, or an anti-inflammatory agent.

9. The method of claim 8, wherein the compound is dexamethasone acetate.

10. The method of claim 1, wherein the matrix comprising the compound is implantable.

11. The method of claim 1, further comprising observing elution at a solution temperature of between 25 and 45 degrees centigrade.

12. The method of claim 1 further comprising agitating the solution with a stirring device.

13. The method of claim 1, wherein the volume of the solution is between 50 and 150 milliliters.

14. The method of claim 1, further comprising using a solution in the method that is selected for its ability to elute at least 50% of dexamethasone acetate impregnated within a polymeric silicon in 72 hours at 45 degrees centigrade.

15. A composition of matter comprising a solution of:
   phosphate buffered saline having a pH range of pH 5 to pH 7;
   1-9% limonene;
   0.3-9% sodium dodecyl sulfate; and
   0.5-15% lower alkanol.

16. The composition of matter of claim 15, wherein the lower alkanol is ethanol or n-butanol.

17. The composition of matter of claim 15, wherein the solution comprises:
   phosphate buffered saline having a pH of 6;
   3-5% limonene;
   3-5% sodium dodecyl sulfate; and
   1-3% n-butanol.

18. The composition of matter of claim 15, further comprising a matrix impregnated with an elutable agent comprising a steroid, an anti-coagulant an antibiotic, or an anti-inflammatory agent.

19. The composition of matter of claim 18, wherein the matrix is a polymer matrix impregnated with dexamethasone acetate.

20. The composition of matter of claim 19, wherein the matrix is adapted for use as part of a cardiac lead.

* * * * *